(12) United States Patent
Fox et al.

(10) Patent No.: US 6,656,920 B2
(45) Date of Patent: Dec. 2, 2003

(54) COMPOSITION AND METHOD FOR PROMOTING ORAL HEALTH

(75) Inventors: Philip C. Fox, Cabin John, MD (US); Martin J. Cummins, Amarillo, TX (US); Joseph M. Cummins, Amarillo, TX (US)

(73) Assignee: Amarillo Biosciences, Inc., Amarillo, TX (US)

( * ) Notice: Subject to any disclaimer, the term of this patent is extended or adjusted under 35 U.S.C. 154(b) by 14 days.

(21) Appl. No.: 09/826,024

(22) Filed: Apr. 4, 2001

(65) Prior Publication Data

US 2001/0046969 A1 Nov. 29, 2001

Related U.S. Application Data

(60) Provisional application No. 60/194,539, filed on Apr. 4, 2000.

(51) Int. Cl.$^7$ .................. A61K 31/715; A61K 31/34
(52) U.S. Cl. ............... 514/53; 514/61; 514/474; 424/55; 424/435; 424/464; 424/465
(58) Field of Search ................ 514/474, 53, 61; 424/55, 435, 464, 465

(56) References Cited

U.S. PATENT DOCUMENTS

| | | | | |
|---|---|---|---|---|
| 4,088,788 A | | 5/1978 | Ream et al. ............... 426/3 |
| 4,816,445 A | * | 3/1989 | Mitsuhashi et al. ........ 514/53 |
| 4,820,506 A | * | 4/1989 | Kleinberg et al. .......... 424/40 |
| 4,822,816 A | | 4/1989 | Markham ................. 514/474 |
| 4,938,963 A | * | 7/1990 | Parnell .................... 424/440 |
| 5,078,989 A | | 1/1992 | Ando et al. ................ 424/62 |
| 5,137,723 A | | 8/1992 | Yamamoto et al. ......... 424/400 |
| 5,496,558 A | | 3/1996 | Napolitano et al. ........ 424/435 |
| 5,614,207 A | | 3/1997 | Shah et al. ................ 424/440 |
| 5,906,811 A | | 5/1999 | Hersh ...................... 424/54 |
| 5,916,371 A | * | 6/1999 | Chaen et al. ................ 127/29 |
| 5,935,584 A | | 8/1999 | Guerrero et al. ........... 424/401 |
| 6,127,409 A | | 10/2000 | Suzuki et al. .............. 514/473 |
| 6,159,459 A | | 12/2000 | Hunter et al. ............ 424/78.08 |
| 6,211,231 B1 | | 4/2001 | Mathur .................... 514/474 |

OTHER PUBLICATIONS

Ester–C product information, Inter–Cal Corporation, 2000.
Halls Defense Vitamin C Supplement Drops product label, Warner–Lambert Company, 1999.

\* cited by examiner

Primary Examiner—Dwayne C. Jones
(74) Attorney, Agent, or Firm—Barnes & Thornburg

(57) ABSTRACT

The present invention relates to a method for increasing unstimulated whole saliva in a patient. The method comprises orally administering an effective amount of a disaccharide, such as maltose, trehalose, or anhydrous crystalline maltose, to the patient in a dosage form such as a lozenge. The disaccharide can also be administered in combination with an effective amount of vitamin C, or a derivative thereof, such as a vitamin C ester. The invention is also directed to a pharmaceutical composition comprising a disaccharide in combination with vitamin C, or a derivative thereof, such as a vitamin C ester. The method is used to treat diseases such as Sjögren's syndrome and xerostomia.

21 Claims, No Drawings

COMPOSITION AND METHOD FOR PROMOTING ORAL HEALTH

CROSS REFERENCE TO RELATED APPLICATIONS

This application claims priority under 35 U.S.C. §119(e) to U.S. Provisional Application Ser. No. 60/194,539, filed Apr. 4, 2000 which is expressly incorporated by reference herein.

FIELD OF THE INVENTION

The present invention relates to a method for treating xerostomia. More particularly, the invention is directed to the use of disaccharides, preferably in lozenge dosage form, for improving production of unstimulated whole saliva in patients in need of such function.

BACKGROUND AND SUMMARY OF THE INVENTION

Sjögren's syndrome is an idiopathic autoimmune disorder characterized by lymphocytic infiltration of multiple organs and tissues, as well as by the presence of autoantibodies, hypergammaglobulinemia, and immunoregulatory abnormalities. Sjögren's syndrome is primarily a disease of women, with nearly 90% of all patients being female. The disease has a typical onset during the fourth or fifth decade of life, and it may be as prevalent as 1 out of every 2,500 females.

Clinically, Sjögren's syndrome presents in either primary or secondary forms. Primary Sjögren's syndrome is characterized by xerostomia (dry mouth) and xerophthalmia (dry eyes) which are the result of a progressive loss of salivary and lacrimal function. Secondary Sjögren's syndrome includes involvement of one or both of these exocrine sites in the presence of another connective tissue disease such as rheumatoid arthritis, systemic sclerosis, or systemic lupus erythematosus. In both primary and secondary forms, there are commonly multiple extraglandular manifestations and serologic evidence of autoimmmunity.

The presence of a focal, periductal mononuclear cell infiltrate is the characteristic histopathologic finding in salivary glands in Sjögren's syndrome. Lymphocytic infiltrates of exocrine glands increase as the inflammatory disease progresses, ultimately producing acinar gland degeneration, necrosis, and atrophy.

Management of the dry eyes and mouth in subjects with Sjögren's syndrome is a daily problem. Dry eyes are treated by protective measures, frequent ophthalmologic evaluations, and wetting agents to sustain a normal ocular surface. The treatment of xerostomia is more difficult. Preventive measures such as supplemental fluoride, avoiding sugar or medications known to cause a dry mouth, and frequent dental checkups are recommended. Artificial saliva or frequent ingestion of non-sugared liquids may provide symptomatic benefit for some subjects. Pharmacologic agents designed to increase salivary flow (secretogogues), including bromhexine, anetholetrithione, pilocarpine, and cevimeline have been tested in subjects with Sjögren's syndrome. They have been shown to increase salivary output transiently, however, none have demonstrated sustained benefit in controlled clinical trials.

Interferons (IFN) have potent antiviral and immunomodulating effects, and five distinct classes of IFN have been designated; alpha ($\alpha$), beta, gamma, omega, and tau. IFN have been shown to enhance phagocytic antigen processing and immune regulatory activity of macrophages, regulate specific cytotoxicity of lymphocytes for target cells, and enhance natural killer cell activity.

The therapeutic utility of IFN-$\alpha$ by the parenteral route has been well established. One natural and two recombinant forms of human IFN are approved for clinical use in the United States in doses ranging from $0.25 \times 10^6$ IU/lesion administered twice weekly in condyloma acuminata up to $36 \times 10^6$ IU given daily in AIDS-related Kaposi's sarcoma. Other approved indications for IFN treatment include hairy cell leukemia, chronic hepatitis B, and chronic hepatitis C. The adverse experiences associated with parenteral IFN appear to be dose related, with the majority of subjects developing one or multiple flu-like symptoms at doses greater than $1 \times 10^6$ IU/day.

The use of high-dose injectable IFN-$\alpha$ for subjects with Sjögren's syndrome was first described in 1993. Shiozawa et al. reported that weekly intramuscular (i.m.) injections of IFN ($1 \times 10^6$ IU/dose) resulted in a significant increase of saliva secretion in subjects with primary Sjögren's syndrome. Ferraccioli et al. successfully treated Sjögren's syndrome subjects with $3 \times 10^6$ IU IFN parenterally three times weekly. These investigators reported significant increases in lacrimal and salivary function with IFN compared to subjects treated with hydroxychloroquine. They also noted improvement in minor salivary gland histopathology on repeat biopsy in 3 of the IFN-treated subjects. Although few subjects experienced adverse effects at these high doses, it is well established that higher doses can cause a consistent and high percent of untoward effects.

Shiozawa and colleagues subsequently examined the potential benefit of natural human IFN-$\alpha$ in low-dose lozenges in two open-label studies. Using 150 IU IFN lozenges three times daily, 5 of 7 subjects and 13 of 24 subjects with Sjögren's syndrome had >30% increase in stimulated whole saliva output after treatment between 9 and 37 weeks (mean duration =22 weeks). Recently, these investigators reported the effectiveness of 150 IU IFN lozenges given TID in 30 subjects with Sjögren's syndrome (28 with the primary form). At 24 weeks, 15 (50%) of 30 subjects treated with 150 IU IFN lozenges TID had a $\geq 100\%$ increase from baseline in stimulated whole salivary flow, compared to only 1 (3%) of 30 control subjects given sucralfate (p<0.001). No clinically significant adverse experiences were reported in this clinical trial. Additionally, the investigators examined minor salivary glands at the completion of the trial in 9 subjects who had responded to treatment with at least a two-fold increase in saliva output. A significant improvement in pathologic changes, including reduced mononuclear infiltration and increased histologically normal epithelial tissue, was found compared to pretherapy biopsies.

Therefore, it appears that low-dose IFN-$\alpha$ administered via the oral-mucosal route may significantly increase salivary secretions in subjects with Sjögren's syndrome without causing the troublesome adverse effects associated with high dose parenteral IFN administration. The purposes of our investigations were to examine the safety and efficacy of four different dosages of IFN lozenges compared to placebo in subjects with primary Sjögren's syndrome over a 12-week period in a Phase 2 trial, and to examine the best dose from our Phase 2 trial in a 24-week Phase 3 trial.

The primary endpoints of our Phase 2 and Phase 3 trials were measurements of unstimulated saliva and stimulated saliva and subjective assessments of dry mouth.

Adequate salivary gland function is critical for protection of the oral cavity and support of oral functions. In humans, saliva is provided by the 3 paired major salivary glands, (parotid, submandibular and sublingual), and thousands of minor salivary glands which are situated throughout the oral cavity and named based on location (buccal, palatal, labial, etc.). Approximately 90% of the day, salivary flow is maintained at a low level of output by endogenous physiologic mechanisms. This is termed unstimulated, or resting, saliva and is essential for general oral comfort and for defense of the oral cavity. The unstimulated saliva is high in antimicrobial and mucoprotective factors. Contrasting with this unstimulated function is the response of the salivary glands to masticatory and gustatory stimuli. During meals, with the stimulation provided by chewing and food flavors, there is a marked increase in salivary output. This stimulated output provides support for swallowing, chewing and buffering of microbial acids, and quickly diminishes when active stimulation ceases.

Since individuals experience their unstimulated saliva flow the great majority of the time, this represents the most important functional state. It also is reflective of the underlying gland health. Generally, an improvement in unstimulated salivary function will be associated with an increase in stimulated salivary capability. Importantly, an increase in unstimulated saliva function provides benefit without any additional action on the part of the patient. This is a great advantage over secretogogues which produce a stimulated saliva for a limited period of time. With an improvement in the underlying unstimulated saliva function, a patient will benefit throughout the day from an increase in salivary factors which modulate microbial populations and coat the oral cavity. This latter activity should aid in speech. It should improve oral comfort, as well, as the mucosa will be better hydrated and protected from insult. This may be accompanied by a decrease in the need for oral comfort agents. Improving unstimulated salivary function results in improving a patient's oral defenses.

The IFN-α was delivered to the patients in 200 mg lozenges consisting of crystalline anhydrous maltose (CAM). The placebo was 200 mg CAM without IFN in both (Phase 2 and Phase 3) clinical trials. After 6 months of daily treatment in our Phase 3 trial, 57 of 90 (63.3%) of placebo-treated patients had an increase in their unstimulated whole saliva (UWS) and 65% of placebo-treated patients wanted to continue therapy with placebo. The IFN-treated group did even better (73% and 81%, respectively), but the beneficial effect of CAM on UWS was striking. Sixty-one (61) of 90 evaluable patients (including 9 of 18 placebo treated patients) in our Phase 2 trial had an increase in their UWS by 12 weeks. Not only will this benefit patients with Sjögren's syndrome, but CAM should benefit people with dry mouth from other causes.

Amid skyrocketing sales of new drugs for treating depression, anxiety and hypertension, doctors and dentists are becoming alarmed about a seemingly innocuous side effect. The problem is dry mouth and its impact can be devastating.

In the absence of saliva, which has potent antibacterial and antiviral properties, bacteria in the mouth run rampant, leading to decay. Users of dry-mouth-causing medications have 10 times the bacteria in their mouths as normal. People with dry mouth also are more prone to fungal infections, gum disease and nutrition problems.

More than 500 drugs list dry mouth as a potential side effect. The biggest culprits are psychiatric drugs—including some old and new brands like Prozac, Paxil, Zoloft, Xanax and Valium—and blood pressure medicines—such as Lopressor and Vasotec. Antihistamines, the new stop-smoking drug Zyban (a repackaging of the antidepressant Wellbutrin), and even some acne medications can also cause dry mouth. Although the drugs contain different chemicals, they can all have a similar effect on the sensitive salivary gland, blocking the body's signal to produce saliva.

A study presented at the International Association of Dental Research in Nice, France, in 1998, reported that 170 patients on certain medications had nearly three time the rate of dental decay as the control group. Patients who were taking psychiatric medicines such as antidepressants and antianxiety drugs had almost four times the rate of decay.

Xerostomia researchers say the biggest problem is that many doctors and dentists aren't aware of the connection between drugs, dry mouth and dental decay. As a result, patients may ignore the side effect, or worse, chew gum or suck candy to abate it, thereby, exposing the teeth to sugar that makes the bacteria grow even more. Our present invention uses only 200 mg of CAM three times a day, thereby, limiting the carcinogenic potential of this therapy, compared to other carbohydrates used in greater amounts.

Maltose is a naturally occurring disaccharide with low cariogenic potential. It is found in many fruits, ranging in concentration from trace amounts to over 2% of the total sugars. In grapes (*Vitis vinifera*), for example, maltose accounts for over 12% of the total soluble solids in the fruit. Maltose is a constituent of many processed foods, also. Three quarters of a cup of spaghetti sauce contains 4 gm of maltose and a cookie approximately 0.5 gm. Twelve ounces of beer have 0.6 gm of maltose. Clearly, maltose intake will be influenced markedly by the particular dietary practices of an individual.

In 1972, an individual's total daily consumption of sugars was estimated to be 200 gm. Of this total, 2.7% is attributed to maltose, for a daily intake in the food supply of 5.4 gm. Additional maltose is generated as a "reversion" product (β-maltose) of glucose during food processing and storage. The amount of this dietary maltose intake has not been calculated. As maltose is a hydrolytic product of starch metabolism, an additional amount of maltose is generated following ingestion of starches. Total daily starch consumption is estimated to be between 135 and 200 gm for an individual. While it is difficult to arrive at a definitive amount, one may extrapolate the amount of maltose generated from starch by referring to standardized starch hydrolysate solutions. For example, a standard maize starch hydrolysate ("glucose syrup") as specified in the US Pharmacopeia, contains 11% maltose. If starch digestion yields approximately 10% maltose, this would add an additional 13.5 to 20 gm of maltose to the diet. Clearly, the 200 mg lozenge consumed three times per day does not add a significant amount of maltose to the diet.

Currently, the USDA Sugars Office does not have consumption data on maltose. The University of Minnesota maintains a nutrient database (NDS) which can be used to determine individual component nutrients in a diet. While maltose figures can be obtained on a specific submitted diet and specific foods, over half of the food maltose values are estimated. Definitive data are not available on maltose consumption at present.

All dietary carbohydrates predispose to dental caries, but sucrose seems to be the most potent in this respect. Substitution of glucose syrup for sucrose in experimental caries studies showed a reduction in decay. We assert that 200 mg lozenges of CAM consumed three times per day will not cause caries.

Caries cannot be induced in germfree animals, no matter how cariogenic the diet on which they subsist. This emphasizes the critical role of the oral bacteria as the principal agent of dental caries. The carbohydrates provide an energy source for the microorganisms.

No one knows exactly how widespread medication-induced dry mouth is, although it is most prevalent in the elderly population. One University of Toronto study found dry mouth in 20% of the elderly patients it surveyed. Another study of 600 elderly Floridians found 39% complaining of dry mouth. Both studies concluded the high rate of dry mouth was associated with using multiple medications. Doctors say increased sales of popular antidepressants and other drugs, as well as the aging population, are expected to lead to a significant increase in the rate of dry mouth.

Dry mouth in older people is particularly worrisome because it can interfere with eating and lead to malnutrition. "Unfortunately, a lot of these medications are life-giving in their potential and they need to be on them," says Frank Astor, chairman of the department of otolaryngology at the Cleveland Clinic Florida, Ft. Lauderdale, and author of a recent study on xerostomia and the elderly.

Doctors say it's important for anyone with chronic dry mouth to see their doctor to be certain the problem is medication-related and not the result of an autoimmune disease. Dry-mouth sufferers can get relief from water, ice chips or sugarless gum or one of several new therapeutic gums, such as Arm & Hammer and Trident Advantage. Foods that are sour or bitter can also stimulate saliva flow. But sufferers generally avoid sugar as well as irritants such as tobacco and alcohol.

More serious dry mouth can be treated with over-the-counter or prescription saliva substitutes. Pilocarpine and cevimeline are saliva-inducing drugs, but they have their own side effects, including excessive sweating.

In one embodiment the invention provides a method for increasing unstimulated whole saliva in a human patient in need of such effect. The method comprises the step of orally administering to said human a composition comprising an effective amount of a disaccharide in the mouth to promote its contact with the oral mucosa.

In another embodiment, the invention provides a method for increasing unstimulated whole saliva in a human patient in need of such effect. The method comprises the step of orally administering to said human a composition comprising an effective amount of a disaccharide in combination with an effective amount of vitamin C, or a derivative thereof, in the mouth to promote contact with the oral mucosa.

In yet another embodiment the invention provides a pharmaceutical composition comprising a disaccharide, vitamin C, or a derivative thereof, and a physiological carrier therefor. The vitamin C derivative may be a vitamin C ester.

DETAILED DESCRIPTION OF THE INVENTION

The present invention is directed to a method for increasing unstimulated whole saliva in a human patient in need of such effect. The method comprises the step of orally administering to said patient a composition comprising an effective amount of a disaccharide in the mouth of a patient to promote its contact with the patient's oral mucosa.

Suitable disaccharides include maltose, lactose, fructose and trehalose. Preferably those disaccharides exhibiting minimal cariogenicity are preferred. Anhydrous crystalline maltose such as the crystalline α-maltose described and claimed in U.S. Pat. No. 4,816,445 (expressly incorporated herein by reference) is preferred.

The disaccharide can be in either liquid or solid lozenge dosage form. Liquid dosage forms are well known in the art. Thus, the dosage form can be in the form of a liquid solution such as a syrup, spray, or other liquid dosage form to be administered and used by the patient in a manner which promotes contact of the disaccharide with oral mucosal tissues, for example, by holding the solution in the mouth for up to one or two minutes. Syrups may be flavored or unflavored and may be formulated using a buffered aqueous solution of the disaccharide as a base with added caloric or non-caloric sweeteners, flavor oils and pharmaceutically acceptable surfactant/dispersants. Other liquid dosage forms, including solutions or sprays containing the disaccharide, can be prepared in a similar manner and can be administered by orally.

Lozenge dosage forms are preferred and can be prepared using art-recognized techniques, for example, by forming compressed tablets/lozenges from tableting compositions comprising the disaccharide. Accordingly, in one embodiment, the solid dosage form is in the form of a lozenge adapted to be dissolved upon contact with saliva in the mouth, with or without the assistance of chewing, to form a saliva solution of the disaccharide.

Lozenges for use in accordance with this invention can be prepared, for example, by art-recognized techniques for forming compressed tablets where the disaccharide is dispersed on a compressible solid carrier, optionally combined with any appropriate tableting aids such as a lubricant (e.g., magnesium-stearate) and is compressed into tablets. The solid carrier component for such tableting formulations can be a saliva-soluble solid, such as a cold water-soluble starch or a monosaccharide, so that the lozenge will readily dissolve in the mouth to release the contained disaccharide acid in saliva solution for contact with and absorption by the oral/pharyngeal mucosa when the lozenge is held in the mouth. The pH of the above-described formulations can range from about 4 to about 8.5.

Lozenges for use in accordance with the present invention can also be prepared utilizing other art-recognized solid unitary dosage formulation techniques. Regardless of the dosage form, liquid or solid, in one preferred embodiment of the present invention the dosage form is held in the patient's mouth for a period of time to promote contact of the disaccharide with the patient's oral mucosa.

Each unit dosage form of disaccharide for use in accordance with this invention includes about 100 to about 1000 mg of disaccharide. The unit dosage forms can be administered several times a day, for example, from 1 to 5 times a day. Good results have been obtained when 200 mg maltose lozenges are administered three times daily.

In another embodiment, the invention is directed to a method for increasing unstimulated whole saliva in a human patient in need of such effect. The method comprises the step of orally administering to said human a composition comprising an effective amount of a disaccharide in combination with an effective amount of vitamin C, or a derivative thereof, in the mouth to promote contact with the oral mucosa.

Accordingly, for the purposes of this invention, combination dosage forms of a disaccharide in combination with vitamin C, or a derivative thereof, are used to increase unstimulated whole saliva. These combination dosage forms can be used to treat such diseases as Sjögren's syndrome and xerostomia.

As used herein, the term "vitamin C" means vitamin C (L-ascorbic acid), and any derivative thereof which exhibits ascorbitic activity as determined by the standard iodine titration test.

The effects of vitamin C include the acceleration of collagen formation, blocking or absorbing UV rays, retardation of melanin formation, enhancement of immune functions, anti-oxidant free-radical scavenging reactions, facilitation of iron absorption, compensation for vitamin E deficiency, and the like. The clinical effects of such metabolic reactions have been widely recognized and reported. For example, the free-radical scavenging effect is believed to enable the body to convert carcinogens to non-toxic derivations which are eliminated in the urine and, consequently, to ameliorate the effects of smoking and exposure of the body to other environmental pollutants. Additionally, animal studies have demonstrated that body enzymes convert vitamin C to oxidation products which have demonstrated tumor growth inhibition. Accordingly, vitamin C has been used in the fields of medical preparations, agricultural chemicals, animal drugs, foods, feeds, cosmetic preparations to benefit skin appearance, and the like.

There is little scientific doubt that the establishment and maintenance of effective levels of vitamin C and its derivatives in the human body yield important health advantages. The presence of vitamin C in substantial concentration has been observed in the adrenals, ovaries, brain, pituitaries, liver, spleen, blood cells, blood serum, and extracellular lung liquids. Most animals have a liver enzyme which enables them to actually mantufacture vitamin C in situ by conversion of blood sugar into ascorbic acid. However, humans do not have this enzyme. As a consequence, the vitamin C which is required by the human body for the various metabolic reactions discussed above must be ingested with the human diet.

Unfortunately, vitamin C is a very unstable substance. Due to its alpha-keto lactone structure, ascorbic acid is very sensitive to the influence of environmental parameters such as light, oxygen, and water. The art has sought to overcome the problem in a variety of ways. One approach is the preparation of ascorbic acid derivatives. These derivatives have greater stability than the parent compound (see, for example, U.S. Pat. Nos. 5,137,723 and 5,078,989).

Such derivatives include, for example, oxidation products such as dehydroascorbic acid and edible salts of ascorbic acid such as, illustratively, calcium, sodium, magnesium, potassium and zinc ascorbates. These derivatives and any other art-recognized vitamin C derivatives, including vitamin C esters, are useful for the purposes of this invention.

The disaccharide in combination with vitamin C, or a derivative thereof, can be in either liquid or solid lozenge dosage form. Lozenge dosage forms are preferred and can be prepared using art-recognized techniques as described above. Regardless of the dosage form, liquid or solid, in one preferred embodiment of the present invention the dosage form including the disaccharide in combination with vitamin C, or a derivative thereof, is held in the patient's mouth for a period of time to promote contact with the patient's oral mucosa.

Each unit dosage form of disaccharide in combination with vitamin C, or a derivative thereof, for use in accordance with this invention includes about 100 to about 1000 mg of disaccharide and about 100 to about 1000 mg of vitamin C, or a derivative thereof. The ratio of disaccharide to vitamin C, or a derivative thereof, in the dosage form is about 10 to 1 to about 1 to 10, more typically about 4 to 1 to about 1 to 4. The unit dosage forms can be administered several times a day, for example, from about 1 to about 5 times a day. Good results have been obtained when the lozenges are administered three times daily.

In yet another embodiment of the invention a pharmaceutical composition is provided. The pharmaceutical composition comprises a disaccharide, vitamin C, or a derivative thereof, and a physiological carrier therefor. The vitamin C derivative may, for example, be a vitamin C ester.

The pharmaceutical composition is adapted for oral administration and may be in an oral dosage form such as the liquid or lozenge dosage forms described above. Such dosage forms and the physiological carriers therefor are well known in the art. The ratios of disaccharide to vitamin C, or a derivative thereof, in the pharmaceutical composition are about 10 to 1 to about 1 to 10, more typically about 4 to 1 to about 1 to 4. The composition is adapted for administration from about 1 to about 5 times a day.

What is claimed is:

1. A method for increasing unstimulated whole saliva in a human patient in need of such effect, said method comprising the step of orally administering to said patient a composition comprising an effective amount of a disaccharide selected from the group consisting of maltose and trehalose and promoting its contact with the patient's oral mucosa.

2. The method of claim 1 wherein the patient suffers from Sjögren's syndrome.

3. The method of claim 1 wherein the patient suffers from a drug induced or radiation induced xerostomia.

4. The method of claim 1 wherein the amount of disaccharide is about 100 mg to about 1 gram per dose.

5. The method of claim 1 wherein the maltose is anhydrous crystalline maltose.

6. The method of claim 5 wherein the disaccharide is in lozenge dosage form.

7. The method of claim 1 wherein the disaccharide is in lozenge dosage form.

8. The method of claim 1 wherein the disaccharide is in a solid or liquid dosage form and the dosage form is held in the patient's mouth for a period of time to promote contact of the disaccharide with the patient's oral mucosa.

9. The method of claim 1 wherein the composition further comprises vitamin C or a derivative thereof.

10. The method of claim 9 wherein the vitamin C derivative is a vitamin C ester.

11. The method of claim 9 wherein the ratio of disaccharide to vitamin C, or a derivative thereof, in the composition is about 10 to 1 to about 1 to 10.

12. A method for increasing unstimulated whole saliva in a human patient in need of such effect, said method comprising the step of orally administering to said patient a composition comprising an effective amount of a disaccharide selected from the group consisting of maltose and trehalose in combination with an effective amount of vitamin C, or a derivative thereof, and promoting its contact with the patient's oral mucosa.

13. The method of claim 12 wherein the patient suffers from Sjögren's syndrome.

14. The method of claim 12 wherein the patient suffers from a drug induced or radiation induced xerostomia.

15. The method of claim 12 wherein the amount of disaccharide is about 100 mg to about 1 gram per dose and the amount of vitamin C, or derivative thereof, is about 100 mg to about 1 gram per dose.

16. The method of claim 12 wherein the maltose is anhydrous crystalline maltose.

17. The method of claim 16 wherein the disaccharide and vitamin C, or derivative thereof, is in lozenge dosage form.

18. The method of claim 12 wherein the vitamin C derivative is a vitamin C ester.

19. The method of claim 12 wherein the disaccharide and vitamin C, or derivative thereof, is in lozenge dosage form.

20. The method of claim 12 wherein the disaccharide in combination with vitamin C, or derivative thereof, is in a solid or liquid dosage form and the dosage form is held in the patient's mouth for a period of time to promote contact with the patient's oral mucosa.

21. The method of claim 12 wherein the ratio of the disaccharide to vitamin C, or a derivative thereof, in the composition is about 10 to 1 to about 1 to 10.

\* \* \* \* \*